United States Patent
Northey

(10) Patent No.: US 10,265,341 B2
(45) Date of Patent: Apr. 23, 2019

(54) HYDROGEL FORMULATION COMPRISING OXIDATIVE REDUCTIVE POTENTIAL WATER

(75) Inventor: Robert Northey, Bellevue, WA (US)

(73) Assignee: Sonoma Pharmaceuticals, Inc., Petaluma, CA (US)

(*) Notice: Subject to any disclaimer, the term of this patent is extended or adjusted under 35 U.S.C. 154(b) by 0 days.

(21) Appl. No.: 13/387,923

(22) PCT Filed: Jul. 30, 2010

(86) PCT No.: PCT/US2010/043978
§ 371 (c)(1),
(2), (4) Date: Mar. 12, 2012

(87) PCT Pub. No.: WO2011/014809
PCT Pub. Date: Feb. 3, 2011

(65) Prior Publication Data
US 2012/0164235 A1 Jun. 28, 2012

Related U.S. Application Data

(60) Provisional application No. 61/230,023, filed on Jul. 30, 2009.

(51) Int. Cl.
| | | |
|---|---|---|
| *A61K 31/74* | (2006.01) | |
| *A61K 47/02* | (2006.01) | |
| *A61K 9/06* | (2006.01) | |
| *A61K 33/00* | (2006.01) | |
| *A61K 33/06* | (2006.01) | |
| *A61K 33/18* | (2006.01) | |
| *A61K 9/00* | (2006.01) | |
| *A61K 45/06* | (2006.01) | |

(52) U.S. Cl.
CPC ............ *A61K 31/74* (2013.01); *A61K 9/0014* (2013.01); *A61K 9/06* (2013.01); *A61K 33/00* (2013.01); *A61K 33/06* (2013.01); *A61K 33/18* (2013.01); *A61K 45/06* (2013.01); *A61K 47/02* (2013.01)

(58) Field of Classification Search
None
See application file for complete search history.

(56) References Cited

U.S. PATENT DOCUMENTS

| | | |
|---|---|---|
| 3,843,548 A | 10/1974 | James |
| 5,876,743 A | 3/1999 | Ibsen et al. |
| 2006/0235350 A1* | 10/2006 | Alimi et al. .................. 604/19 |
| 2006/0241002 A1 | 10/2006 | Rogozinski |
| 2008/0255498 A1* | 10/2008 | Houle .................. 604/20 |
| 2009/0068255 A1* | 3/2009 | Yu et al. ...................... 424/450 |
| 2014/0134277 A1 | 5/2014 | Panicheva et al. |
| 2017/0100331 A1* | 4/2017 | Klein .................. A61K 31/167 |

FOREIGN PATENT DOCUMENTS

| | | |
|---|---|---|
| WO | WO 03/048421 A1 | 6/2003 |
| WO | WO 05/065383 A1 | 7/2005 |

OTHER PUBLICATIONS

Handbook of Cosmetic and Personal Care Additives, 1st, Ash et al. at pages including title, contents, pp. 602 and pp. 760, (1994).*
Ash et al., "Handbook of Cosmetic and Personal Care Additives," Grower Publishing Limited, Hampshire, England, 1994. See, title, contents, pp. 602, 760.
U.S. Patent & Trademark Office, International Search Report in International Application No. PCT/US2010/043978 (dated Sep. 16, 2010).
European Patent Office, Extended European Search Report in European Patent Application No. 10 80 5132 (dated Jan. 29, 2014).
European Patent Office, Third Party Observations in European Patent Application No. 10 80 5132 (dated Oct. 2, 2014).
"Onset Dermatologics Launches Patented Aurstat® Anti-Itch Hydrogel 225ml," Press Release, Onset Dermatologics, May 6, 2013 http://www.onsetdermatologics.com/newsroom/press-release/2013/05/onset-dermatologies-launches-patented—aurstat.
"Aurstat® Anti-Itch Hydrogel," *USGovXML* FDA Label http://usgovxml.com/mobile/FDALabelXML.aspx?source=http://usgovxml.com/DailyMed/2013/05/08/193475dc-df01-43e3-b9a4-d5f2b609b336.xml.

* cited by examiner

*Primary Examiner* — Ernst V Arnold
*Assistant Examiner* — Kyung S Chang
(74) *Attorney, Agent, or Firm* — Leydig, Voit & Mayer, Ltd.

(57) ABSTRACT

The present invention relates to a hydrogel formulation containing an oxidative reduction potential (ORP) water solution and a gelling agent. The invention further provides a method for treating or preventing a condition in a patient comprising topically administering to a patient a therapeutically effective amount of a hydrogel formulation comprising an oxidative reductive potential solution and a gelling agent. A method for promoting wound healing in a patient is also provided.

5 Claims, No Drawings

HYDROGEL FORMULATION COMPRISING OXIDATIVE REDUCTIVE POTENTIAL WATER

CROSS-REFERENCE TO RELATED APPLICATIONS

This patent application is the U.S. national phase of International Application No. PCT/US2010/043978, filed on Jul. 30, 2010, which claims the benefit of U.S. Provisional Application No. 61/230,023, filed Jul. 30, 2009, the disclosures of which are incorporated herein by reference in their entireties for all purposes.

FIELD OF THE INVENTION

The present invention pertains to hydrogel formulations for topical administration comprising an oxidative reductive potential (ORP) water solution, methods for the production thereof, and methods for treating and preventing a variety of conditions using such formulations.

BACKGROUND OF THE INVENTION

Oxidative reductive potential (ORP) water, also known as super-oxidized water, can be used as a non-toxic disinfectant to eradicate microorganisms, including bacteria, viruses and spores, in variety of settings. ORP water has applications in wound care, medical device sterilization, food sterilization, hospitals, consumer households and anti-bioterrorism. Advantageously, ORP water is environmentally safe and, thus, avoids the need for costly disposal procedures.

Although ORP water is an effective disinfectant, it has an extremely limited shelf-life, usually only a few hours. As a result of this short lifespan, the production of ORP water must take place in close proximity to where ORP water is to be used as a disinfectant. This means that a healthcare facility, such as a hospital, must purchase, house and maintain the equipment necessary to produce ORP water. Additionally, prior manufacturing techniques have not been able to produce sufficient commercial-scale quantities of ORP water to permit its widespread use as a disinfectant at healthcare facilities.

In addition, common delivery forms for the topical administration of ORP water tend to be inherently problematic. Such ORP compositions are generally administered in the form of either a liquid or a gel, both of which have innate disadvantages. The application of liquid products to treatment sites is difficult to control, as run-off, spillage, and poor containment are commonly encountered problems. In contrast, thick gels are not easily dispensed, and may not reach the entire surface area of wounds as easily as liquids.

Accordingly, a need exists for ORP water formulations that are stable over an extended period of time and are suitable for effective topical administration. The present invention provides such formulations. These and other advantages of the invention, as well as additional inventive features, will be apparent from the description of the invention provided herein.

BRIEF SUMMARY OF THE INVENTION

The present invention provides a hydrogel formulation for topical administration comprising an oxidative reductive potential (ORP) water solution and a metal silicate gelling agent. In one embodiment, the metal silicate gelling agent is present in an amount of from about 1.0 weight-percent to about 5.0 weight-percent and the buffering agent is present in an amount of from about 0.1 weight-percent to about 1.0 weight-percent, wherein the formulation is stable for at least two months, has a pH from about 5.0 to about 8.5, and has a viscosity of about 1,000 centipoise (cP) to about 20,000 cP.

The present invention further provides a method for treating or preventing a condition in a patient comprising topically administering to a patient a therapeutically effective amount of a hydrogel formulation comprising an ORP solution and a metal silicate gelling agent.

In addition, the present invention also relates to a method for promoting wound healing in a patient comprising applying to a wound a therapeutically effective amount of a hydrogel formulation comprising an ORP water solution and a metal silicate gelling agent.

DETAILED DESCRIPTION OF THE INVENTION

In accordance with the present invention, the hydrogel formulations for topical administration comprise an oxidative reductive potential (ORP) water solution and a gelling agent. The inventive hydrogel formulations disclosed herein provide enhanced efficacy and stability.

As used herein, and as understood by those of skill in the art, the term "hydrogel" refers to any naturally-occurring or synthetic hydrophilic material capable of retaining high percentages of water within its structure, while not dissolve in the water. In other words, a hydrogel is a gel wherein water is the dispersion medium for a matrix of water-swellable polymer or colloid particles. Typically, hydrogels swell in aqueous solution to an equilibrium volume and maintain their shape.

The amount of ORP water present in the hydrogel formulations of the invention is generally from about 10 weight-percent to about 99 weight-percent, based on the total weight of the formulation. In one aspect, the amount of ORP water present is from about 60 weight-percent to about 99 weight-percent. In a preferred embodiment, the amount of ORP water present in the inventive hydrogel formulations is from about 85 weight-percent to about 99 weight-percent.

The ORP water solution included in the hydrogel formulations of the present invention may be acidic, neutral, or basic, and generally has a pH from about 1 to about 14. At this pH, the ORP water solution can safely be applied in suitable quantities to hard surfaces without damaging the surfaces or harming objects, such as human skin, that comes into contact with the ORP water solution. Typically, the pH of the ORP water solution is from about 3 to about 8. More preferably, the pH of the ORP water solution is from about 6.2 to about 7.8.

The ORP water solution included in the hydrogel formulations of the present invention generally has an oxidation-reduction potential of between −1000 millivolts (mV) and +1150 millivolts (mV). This potential is a measure of the tendency (i.e., the potential) of a solution to either accept or transfer electrons that is sensed by a metal electrode and compared with a reference electrode in the same solution. This potential may be measured by standard techniques including, for example, by measuring the electrical potential in millivolts of the ORP water solution relative to standard reference silver/silver chloride electrode. The ORP water generally has a potential between −400 mV and +1300 mV. Preferably, the ORP water solution has a potential between 0 mV and +1250 mV, and more preferably between +500 mV and +1250 mV. Even more preferably, the ORP water of the present invention has a potential of between +800 mV and +1100 mV, and most preferably between +800 mV and +1000 mV.

Various ionic and other species may be present in the ORP water solution. For example, the ORP water solution may contain free chlorine. Free chlorine typically includes, but is not limited to, hypochlorous acid (HClO), hypochlorite ions (ClO$^-$), sodium hypochlorite (NaOCl), dissolved chlorine gas (Cl$_2$), and other radical chlorine species. Typically, the total amount of free chlorine species present in the ORP water solution is greater than about 10 parts per million (ppm) and is generally present, for example, in levels of about 10 ppm to about 400 ppm. In one embodiment of the present invention, the free chlorine species are present in an amount of about 50 ppm to about 200 ppm, preferably about 80 ppm to about 170 ppm, and more preferably about 100 ppm to about 150 ppm, and most preferably about 120 ppm to about 130 ppm.

The ratio of hypochlorous acid to hypochlorite ion is dependent upon pH. Temperature also impacts the ratio of the free chlorine component. In one embodiment, when the ORP water solution has a pH of 7.4, hypochlorous acid levels are typically from about 5 ppm to about 75 ppm. In another embodiment, hypochlorous acid is present in the ORP water solution in an amount of about 5 ppm to about 35 ppm. The amount of sodium hypochlorite is generally in the range of about 0.1 ppm to about 50 ppm.

The chlorine content may be measured by methods known in the art, such as the DPD colorimeter method (Lamotte Company, Chestertown, Md.) or other known methods established by the Environmental Protection Agency. In the DPD colorimeter method, a yellow color is formed by the reaction of free chlorine with N,N-diethyl-p-phenylenediamine (DPD) and the intensity is measured with a calibrated calorimeter that provides the output in parts per million. Further addition of potassium iodide turns the solution a pink color to provide the total chlorine value.

The ORP water solution included in the hydrogel formulations of the present invention is generally stable for at least twenty-hours, and typically at least two days. More typically, the ORP water solution is stable for at least one week (e.g., one week, two weeks, three weeks, four weeks, etc.), and preferably at least two months. More preferably, the ORP water solution is stable for at least six months after its preparation. Even more preferably, the ORP water solution is stable for at least one year, and most preferably for at least three years.

As used herein, the term "stable" generally refers to the ability of the ORP water solution to remain suitable for its intended use, for example, in decontamination, disinfection, sterilization, anti-microbial cleansing, and wound cleansing, for a specified period of time after its preparation under normal storage conditions (i.e., room temperature). The ORP water solution of the invention is also stable when stored under accelerated conditions. For example, the ORP water solution is stable when stored at about 30° C. to about 60° C., for at least 90 days, and preferably 180 days.

The concentrations of ionic and other species present in the ORP water solution are generally maintained during the shelf-life of the ORP water solution. Typically, the concentrations of the free chlorine species present in the ORP water solution are maintained at about 70% or greater from their initial concentration for at least two months after preparation of the ORP water solution. Preferably, these concentrations are maintained at about 80% or greater of their initial concentration for at least two months after preparation of the ORP water solution. More preferably, these concentrations are at about 90% or greater of their initial concentration for at least two months after preparation of the ORP water solution, and most preferably, about 95% or greater.

The stability of the ORP water solution included in the hydrogel formulations of the present invention may be determined based on the reduction in the amount of organisms present in a sample following exposure to the ORP water solution. The measurement of the reduction of organism concentration may be carried out using any suitable organism including bacteria, fungi, yeasts, or viruses. Suitable organisms include, but are not limited to, *Escherichia coli, Staphylococcus aureus, Candida albicans*, and *Bacillus athrophaeus* (formerly *B. subtilis*). The ORP water solution is useful as both a low-level disinfectant capable of a four log (10$^4$) reduction in the concentration of live microorganisms and a high-level disinfectant capable of a six log (10$^6$) reduction in concentration of live microorganisms.

In one aspect of the invention, the ORP water solution is capable of yielding at least a four log (10$^4$) reduction in total organism concentration following exposure for one minute, when measured at least two months after preparation of the solution. Preferably, the ORP water solution is capable of such a reduction of organism concentration when measured at least six months after preparation of the solution. More preferably, the ORP water solution is capable of such a reduction of organism concentration when measured at least one year after preparation of the ORP water solution, and most preferably when measured at least three years after preparation of the ORP water solution.

In another aspect of the invention, the ORP water solution is capable of at least a six log (10$^6$) reduction in the concentration of a sample of live microorganisms selected from the group consisting of *Escherichia coli, Pseudomonas aeruginosa, Staphylococcus aureus* and *Candida albicans* within one minute of exposure, when measured at least two months after preparation of the ORP water solution. Preferably, the ORP water solution is capable of achieving this reduction of *Escherichia coli, Pseudomonas aeruginosa, Staphylococcus aureus* or *Candida albicans* organisms when measured at least six months after preparation, and more preferably at least one year after preparation. Preferably, the ORP water solution is capable of at least a seven log (10$^7$) reduction in the concentration of such live microorganism within one minute of exposure, when measured at least two months after preparation.

The ORP water solution included in the hydrogel formulations of the present invention is generally capable of reducing a sample of live microorganisms including, but not limited to, *Escherichia coli, Pseudomonas aeruginosa, Staphylococcus aureus* and *Candida albicans*, from an initial concentration of between about 1×10$^6$ and about 1×10$^8$ organisms/ml to a final concentration of about zero organisms/ml within one minute of exposure, when measured at least two months after preparation of the ORP water solution. This is between a six log (10$^6$) and eight log (10$^8$) reduction in organism concentration. Preferably, the ORP water solution is capable of achieving this reduction of *Escherichia coli, Pseudomonas aeruginosa, Staphylococcus aureus* or *Candida albicans* organisms when measured at least six months after preparation, and more preferably at least one year after preparation.

Alternatively, the ORP water solution is capable of a six log (10$^6$) reduction in the concentration of a spore suspension of *Bacillus* athrophaeus spores within about five minutes of exposure, when measured at least two months after preparation of the ORP water solution. Preferably, the ORP water solution is capable of achieving this reduction in the concentration of *Bacillus athrophaeus* spores when measured at least six months after preparation, and more preferably at least one year after preparation.

The ORP water solution is further capable of a four log ($10^4$) reduction in the concentration of a spore suspension of *Bacillus athrophaeus* spores within about thirty (30) seconds of exposure, when measured at least two months after preparation of the ORP water solution. Preferably, the ORP water solution is capable of achieving this reduction in the concentration of *Bacillus athrophaeus* spores when measured at least six months after preparation, and more preferably at least one year after preparation.

The ORP water solution is also capable of a six log ($10^6$) reduction in the concentration of fungal spores, such as *Aspergillis niger* spores, within about five to about ten minutes of exposure, when measured at least two months after preparation of the ORP water solution. Preferably, the ORP water solution is capable of achieving this reduction in the concentration of fungal spores when measured at least six months after preparation, and more preferably at least one year after preparation.

The production of the ORP water solution is carried out by an oxidation-reduction process, also referred to as an electrolytic or redox reaction, in which electrical energy is used to produce chemical change in an aqueous solution. Electrical energy is introduced into and transported through water by the conduction of electrical charge from one point to another in the form of an electrical current. In order for the electrical current to arise and subsist there must be charge carriers in the water, and there must be a force that makes the carriers move. The charge carriers can be electrons, as in the case of metal and semiconductors, or they can be positive and negative ions in the case of solutions.

The ORP water solution used in the present invention may be prepared by any suitable means. In one embodiment, the ORP water solution is produced using at least one electrolysis cell comprising an anode chamber, cathode chamber and salt solution chamber located between the anode and cathode chambers, as set forth in International Application WO 05/065383 A1, the disclosure of which is herein incorporated by reference. In such a process, a reduction reaction occurs at the cathode while an oxidation reaction occurs at the anode. The specific reductive and oxidative reactions that are believed to occur are described in International Application WO 03/048421 A1, the disclosure of which is herein incorporated by reference.

As used herein, water produced at an anode is referred to as anode water and water produced at a cathode is referred to as cathode water. Anode water contains oxidized species produced from the electrolytic reaction while cathode water contains reduced species from the reaction. Anode water generally has a low pH typically from about 1 to about 6.8. Anode water generally contains chlorine in various forms including, for example, chlorine gas, chloride ions, hydrochloric acid and/or hypochlorous acid. Oxygen in various forms is also present including, for example, oxygen gas, peroxides, and/or ozone. Cathode water generally has a high pH typically from about 7.2 to about 11. Cathode water generally contains hydrogen gas, hydroxyl radicals, and/or sodium ions.

The ORP water solution included in the hydrogel formulation of the present invention preferably comprises a combination of anode water and cathode water. In this regard, cathode water is generally present in the ORP water solution in an amount of from about 10% by volume to about 90% by volume of the solution. Preferably, cathode water is present in the ORP water solution in an amount of from about 10% by volume to about 50% by volume, more preferably of from about 20% by volume to about 40% by volume of the solution, and most preferably of from about 20% by volume to about 30% by volume of the solution. Additionally, anode water may be present in the ORP water solution in an amount of from about 50% by volume to about 90% by volume of the solution.

In addition to the ORP water solution, the hydrogel formulation for topical administration according to the present invention further comprises a metal silicate gelling agent. The metal silicate gelling agent can increase the viscosity of an ORP water solution sufficiently to yield a gel or semisolid product.

Any suitable metal silicate gelling agent may be used in the hydrogel formulation of the present invention. Typically, a metal silicate gelling agent is used, wherein the metal is an alkali metal, an alkaline earth metal, or a combination thereof. Suitable alkali metals or alkaline earth metals include, but are not limited to, lithium, sodium, potassium, magnesium, calcium, and the like. In a preferred embodiment, the metal silicate gelling agent is a sodium magnesium silicate or a derivative thereof. In a most preferred embodiment, the metal silicate gelling agent is sodium magnesium fluorosilicate.

The gelling agent can be present in the inventive hydrogel formulation in any suitable amount. Generally, the amount of gelling agent is from about 0.1% by weight to about 10% by weight, based on the weight of the formulation. Preferably, the amount of gelling agent is from about 1.0% to about 5% by weight.

The hydrogel formulation of the present invention my optionally include a buffering agent. Any suitable buffering agent may be employed to yield and maintain the desired pH of the formulation. Buffers suitable for use in the hydrogel formulations described herein include, but are not limited to, salts and acids of acetate, glutamate, citrate, tartrate, benzoate, lactate, histidine or other amino acids, gluconate, phosphate, malate, succinate, formate, propionate, and carbonate. Other buffering agents are generally known in the art (see, e.g., *Handbook of Cosmetic and Personal Care Additives,* 2nd ed., Ashe et al. eds. (2002), and *Handbook of Pharmaceutical Excipients,* 4th ed., Rowe et al. eds. (2003)). Suitable buffering agents may be either in liquid or solid form. In a preferred embodiment, the buffering agent is an acid or salt of a phosphate compound. In a more preferred embodiment, the buffering agent is sodium phosphate. The sodium phosphate employed herein can be any suitable form of sodium phosphate including, for example, monobasic sodium phosphate, dibasic sodium phosphate, or combinations thereof.

When present, any suitable amount of buffering agent may be included in the formulation of the invention. Generally, the amount of buffering agent present in the inventive hydrogel formulations is from about 0.01 weight-percent to about 5.0 weight-percent, based on the weight of the formulation. Preferably, the buffering agent is present in an amount of from about 0.1 weight-percent to about 1.0 weight-percent.

The hydrogel formulations may further contain additional components such as colorants, fragrances, buffers, physiologically acceptable carriers and/or excipients, and the like. Examples of suitable colorants include, but are not limited to, titanium dioxide, iron oxides, carbazole violet, chromium-cobalt-aluminum oxide, 4-Bis[(2-hydroxyethyl)amino]-9,10-anthracenedione bis(2-propenoic)ester copolymers, and the like. Any suitable fragrance can be used.

The formulation of the invention may be prepared by any suitable means. The components of the formulation, such as the ORP water solution and gelling agent, may be mixed together in any manner to yield a hydrogel. When the gelling agent is in the form of a power, it may first be sieved to break up large agglomerates to allow for the preparation of a hydrogel formulation. Preferably, the components are mixed together for using an electric mixture or other suitable device to ensure uniformity. The ORP water solution and the gelling agent of the formulation are generally mixed from about 400 rpm to about 1000 rpm, preferably from about 500 rpm to about 800 rpm, and more preferably from about 500 rpm to about 600 rpm. The ORP water solution and the gelling agent are mixed for a sufficient period of time to yield a hydrogel, generally from about 1 minute to about 2 hours after the components have been combined.

A buffering agent, such as sodium phosphate, may subsequently be added to the hydrogel formulation containing the ORP water solution and gelling agent and the pH of the product can be adjusted to its final value using, for example, hydrochloric acid and/or sodium hydroxide.

The physical properties of the hydrogel formulation of the present invention are typically the same as those of the ORP water solution included in the formulation. The properties of the ORP water solution remain even after the addition of a gelling agent and optional buffering agent. For example, the pH of the ORP water solution itself and the hydrogel formulation containing the ORP water solution are generally the same. Accordingly, all of the characteristics of the ORP water solution described herein apply to the hydrogel formulation of the invention.

The pH of the hydrogel formulation of the present invention is generally from about 3 to about 9. Typically, the pH of the hydrogel formulation is from about 5.0 to about 8.5. Preferably, the pH of the hydrogel formulation is from about 5.6 to about 8.0. More preferably, the pH of the hydrogel formulation is from about 6.2 to about 7.8. Even more preferably, the pH of the hydrogel formulation is from about 6.6 to about 7.1.

The viscosity of the hydrogel formulation can be any suitable viscosity such that the formulation can be topically administered to a patient. In one embodiment, the viscosity of the hydrogel formulation is in the range of about 1,000 to about 100,000 centipoise (cP). More particularly, the viscosity of the hydrogel is about 1,000 cP, about 2,000 cP, about 3,000 cP, about 4,000 cP, about 5,000 cP, about 10,000 cP, about 15,000 cP, about 20,000 cP, about 25,000 cP, about 30,000 cP, about 35,000 cP, about 40,000 cP, about 45,000 cP, about 50,000 cP, about 55,000 cP, about 60,000 cP, about 65,000 cP, about 70,000 cP, about 75,000 cP, about 80,000 cP, about 85,000 cP, about 90,000 cP, about 95,000 cP, or ranges thereof). Preferably, the viscosity of the hydrogel is in the range of about 1,000 cP to about 20,000 cP. More preferably, the viscosity of the hydrogel is in the range of about 12,000 cP to about 20,000 cP.

The stability of the hydrogel formulation of the present invention is generally the same as the stability of the ORP water solution. Accordingly, the hydrogel formulation is generally stable for at least twenty-hours, and typically at least two days. More typically, the formulation is stable for at least one week (e.g., one week, two weeks, three weeks, four weeks, etc.), and preferably at least two months. More preferably, the formulation is stable for at least six months after its preparation. Even more preferably, the formulation is stable for at least one year, and most preferably for at least three years.

The stability characteristics of the ORP water solution described herein apply to the hydrogel formulation. Alternatively, the stability of the hydrogel formulation may be determined by various physical characteristics including, for example, free available chlorine (FAC), pH, viscosity and appearance.

By way of example, the hydrogel formulation may have one or more of the following attributes properties following storage for at least 18 months: FAC greater than about 10.0 ppm; pH of about 6.2 to about 7.8; viscosity of about 12,000 to about 20,000 cP; fill volume of not less than about 60 g; and suitable appearance (clear colorless gel) and package integrity (no visible signs of leakage).

Following its preparation, the hydrogel formulation of the present invention may be transferred to a sealed container for distribution and sale to end users such as, for example, health care facilities including hospitals, nursing homes, doctor offices, outpatient surgical centers, dental offices, and the like. The pharmaceutical dosage form according to the present invention comprises the formulation for topical administration as described herein and a sealed container into which the formulation is placed.

Any suitable sealed container may be used that maintains the sterility and stability of the formulation held by the container. The container may be constructed of any material that is compatible with the components of the formulation, for example, the ORP water solution and the gelling agent. The container should be generally non-reactive so that the ions present in the ORP water solution do not react with the container to any appreciable extent.

Preferably, the container is constructed of plastic or glass. The plastic may be rigid so that the container is capable of being stored on a shelf. Alternatively, plastic may be flexible, such as a flexible bag.

Suitable plastics include polypropylene, polyester terephthalate (PET), polyolefin, cycloolefin, polycarbonate, ABS resin, polyethylene, polyvinyl chloride, and mixtures thereof. Preferably, the container comprises polyethylene selected from the group consisting of high-density polyethylene (HDPE), low-density polyethylene (LDPE), and linear low-density polyethylene (LLDPE). Most preferably, the container is high density polyethylene.

The container has an opening to permit dispensing of the formulation for administration to a patient. The container opening may be sealed in any suitable manner. For example, the container may be sealed with a twist-off cap or stopper. Optionally, the opening may be further sealed with a foil layer.

The headspace gas of the sealed container may be air or other suitable gas that does not react with the ORP water solution or other components of the formulation. Suitable headspace gases included nitrogen, oxygen, and mixtures thereof.

The hydrogel formulation of the present invention is suitable for topical administration to a patient, including a human and/or animal, to treat a variety of conditions. Specifically, the formulation may be applied to animals (e.g., mice, rats, pigs, cows, horses, dogs, cats, rabbits, guinea pigs, hamsters, birds) and humans. Topical administration includes application to the skin as well as oral, intranasal, intrabronchial, and rectal routes of administration.

In one embodiment, the present invention is directed to a method for treating a condition in a patient by topically administering a formulation comprising an ORP water solution and a gelling agent.

Conditions in a patient that may be treated according to the invention include, for example, the following: surgical/ open wound cleansing agent; skin pathogen disinfection (e.g., for bacteria, mycoplasmas, virus, fungi, prions); wound disinfection (e.g., battle wounds); wound healing promotion; burn healing promotion; treatment of skin fungi; psoriasis; athlete's foot; ear infections (e.g., swimmer's ear); traumatic wounds; acute, subchronic and chronic infections (e.g. diabetic foot infections being an example of the latter), pressure ulcers, derma-abrasion, debrided wounds, laser re-surfacing, donor sites/grafts, exuding partial and full thickness wounds, superficial injuries (lacerations, cuts, abrasions, minor skin irritations) and other medical applications on or in the human or animal body. Ulcers treated according to the invention may or may not have abscesses or necrotic tissue present.

Additionally, the invention is directed to a method for promoting wound healing in a patient by applying to a wound a hydrogel formulation comprising an oxidative reductive potential water solution and a gelling agent. The wound to be treated may be caused by any surgery, ulcer or other means. Ulcers that may be treated include, for example, diabetic foot ulcers.

The present invention further relates to a method for preventing a condition in a patient by topically administering a hydrogel formulation comprising an ORP water solution and a gelling agent. For example, the hydrogel formulation can be used as a barrier on open wounds to prevent infection. Specifically, the hydrogel formulation can be applied to the surface of a wound, such as a foot ulceration in a diabetic, who is prone to neurological and vascular complications. The formulation applied thusly can provide a barrier to infection, since these wounds are the principal portal for infection for diabetic patients.

The formulation may be used to prevent sexually transmitted diseases in a patient including, for example, infections. Such infections that may be prevented include herpes, human immunodeficiency virus (HIV) and vaginal infections. The hydrogel formulation also may be used as a spermicide.

While not being bound to any particular theory, and in no way limiting the present invention, it is believed that the ORP water solution contained in the hydrogel formulation eradicates the bacteria with which it contacts by destroying the bacterial cellular components such as proteins and DNA.

The hydrogel formulation of the present invention may be used or applied in a therapeutically effective amount to provide the desired therapeutic effect on bacteria, viruses, and/or germs. As used herein, a therapeutically effective amount refers to an amount of the formulation that results in an improvement of the condition being treated or to be prevented. For example, when used to treat an infection, a therapeutically effective amount of the formulation reduces the extent of the infection and/or prevents further infection. As is appreciated by one skilled in the art, the efficacy of the formulation of the invention resulting from administering the formulation may be short-term (i.e., a few days) and/or long-term (e.g., months).

The hydrogel formulation may further be applied over a sufficient period of time, for example, one two, several days, one week, or several weeks, until the desired effect on the patient is observed.

The hydrogel formulation may be applied in any suitable manner. For example, a quantity of the formulation may be applied to the surface of the patient to be treated and then evenly spread using the patient's own fingers. Alternatively, a health care provider may apply the formulation to the patient's tissue. A suitable implement, for example, a disposable wipe or cloth, may be used to apply the inventive hydrogel formulation.

The following examples further illustrate the invention but, of course, should not be construed as in any way limiting its scope.

Example 1

This example demonstrates a hydrogel formulation of the invention suitable for topical administration to a patient. The formulation contains the following:

| Component | Concentration (weight-percent) |
|---|---|
| ORP Water Solution: | |
| water | 96.5330% |
| sodium chloride | 0.0660% |
| sodium hypochlorite | 0.0002% |
| hypochlorous acid | 0.0008% |
| Sodium Magnesium Fluorosilicate | 3.000% |
| Sodium Phosphate | 0.400% |

The above clear, colorless hydrogel formulation was analyzed in accordance with the methods described herein to determine the physical properties and levels of ionic and other chemical species present. As such, it was determined that the hydrogel formulation had a pH of 6.2 to 7.8, a viscosity of 12,000 cP to 20,000 cP, and a free available chlorine concentration of 120-130 ppm.

Example 2

This example describes the manufacture of the hydrogel formulation of Example 1.

Prior to gel manufacture, a reaction vessel was heated to a temperature of 50° C. Once heated, the ORP water solution was transferred into the reactor and allowed to reach an equilibrium temperature of 50° C., while mixing. The gelling agent (sodium magnesium fluorosilicate) was then slowly added to the solution until a concentration of 3%, by weight, was reached. The combined product was allowed to mix for 1 hour to fully develop into a gel. Buffering agent (monobasic sodium phosphate) was then added at a concentration of 0.4%, by weight, and the product was mixed for 30 minutes. The pH of the resulting product was adjusted to its final value using hydrochloric acid, and was mixed for an additional 30 minutes.

Example 3

This example demonstrates the stability of the hydrogel formulation of Example 1.

Specifically, the hydrogel formulation of Example 1 was sealed in a 2 oz. PET Bottle with a PP Disc-Top Cap and subjected to stability studies under accelerated (at 40° C.) and real time (at 22° C.) conditions.

In the accelerated aging studies (40° C.), samples were tested every week for the first four weeks, every other week for the next four weeks and then monthly until the free available chlorine (FAC) dropped below 10 ppm. Samples were tested in a Validated Environmental Test Chamber set at 40° C.±2° C. In order to ensure product exposure to both the PET bottle and the PP Cap, samples were placed into the chamber lying on their sides. Each data point was represented by an unopened bottle. One sample was tested at each time point for the following attributes: Free Available Chlorine (FAC), pH, and viscosity.

In the real time aging study (22° C.), samples were tested after storage for three months. Samples were tested in an Environmental Test Chamber set at 22° C.±2° C. In order to ensure product exposure to both the PET bottle and the PP Cap, samples were placed into the chamber lying on their sides. Each data point was represented by an unopened bottle. One sample was tested at each time point for the following attributes: Free Available Chlorine (FAC), pH, and viscosity.

As is demonstrated below, the hydrogel formulation of the present invention is stable for at least 18 months when stored in a 2 oz. PET Bottle with a PP Disc-Top Cap.

TABLE 1

Accelerated (40° C.) Stability Data

| 40° C. | Test | FAC | pH | Viscosity |
|---|---|---|---|---|
| | Acceptance Criteria | >10.0 ppm | 6.2-7.8 | 12,000-20,000 |
| Time (month @ 40° C.) | Adjusted Time (months @ 22° C.) | ppm | pH units | cP |
| 0 | 0 | 126.3 | 6.6 | 15000 |
| 0.1 | 1 | 117.3 | 6.8 | 15000 |
| 0.2 | 1 | 110.9 | 6.9 | 13500 |
| 0.4 | 2 | 105.9 | 6.9 | 13500 |
| 0.5 | 3 | 97.9 | 7.0 | 15500 |
| 0.6 | 3 | 95.9 | 6.9 | 15500 |
| 0.7 | 4 | 89.7 | 6.9 | 15500 |
| 0.8 | 5 | 89.3 | 7.0 | 15250 |
| 0.9 | 5 | 82.0 | 7.0 | 15750 |
| 1.4 | 8 | 67.2 | 7.0 | 16000 |
| 1.7 | 10 | 49.7 | 6.9 | 16500 |
| 2.2 | 13 | 39.5 | 7.1 | 16500 |
| 2.6 | 15 | 21.0 | 7.1 | 17000 |
| 3.6 | 21 | 8.0 | 7.1 | 17750 |

TABLE 2

Real Time (22° C.) Stability Data

| 22° C. | Test | FAC | pH | Viscosity |
|---|---|---|---|---|
| | Acceptance Criteria | >10.0 ppm | 6.2-7.8 | 12,000-20,000 |
| Time (months) | Adjusted Time (N/A) | ppm | pH units | cP |
| 0 | N/A | 126.3 | 6.6 | 15000 |
| 3 | N/A | 97.1 | 7.1 | 14250 |
| 6 | N/A | 82.3 | 7.1 | 15000 |

The results of the stability studies indicate that the hydrogel formulation of the present invention is stable for at least 18 months when stored in a 2 oz. PET Bottle with a PP Disc-Top Cap.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A hydrogel formulation for topical administration comprising an oxidative reductive potential (ORP) water solution, wherein the formulation has a pH of from about 6.2 to about 7.8, wherein the oxidative reductive potential water solution has a total amount of free chlorine species of about 10 ppm to about 400 ppm, wherein the free chlorine species is hypochlorous acid, hypochlorite ion, sodium hypochlorite, chloride ion, or dissolved chlorine gas, about 3.0% by weight of sodium magnesium fluorosilicate, and about 0.4% by weight of sodium phosphate, wherein the concentrations of the free chlorine species present in the formulation are maintained at about 70% or greater from their initial concentration for at least two months, the viscosity of the formulation is maintained in a range of about 12000 cP to about 20000 cP for at least 18 months after preparation of the formulation, and the pH of the formulation is maintained in a range of about 6.2 to about 7.8 for at least 18 months after preparation of the formulation.

2. The formulation of claim 1, wherein the concentrations of the free chlorine species present in the formulation are maintained at about 70% or greater from their initial concentration for at least one year.

3. A method for disinfecting a wound in a patient comprising topically administering to a patient a therapeutically effective amount of a hydrogel formulation comprising an oxidative reductive potential water solution, wherein the formulation has a pH of from about 6.2 to about 7.8, wherein the oxidative reductive potential water solution has a total amount of free chlorine species of about 10 ppm to about 400 ppm, wherein the free chlorine species is hypochlorous acid, hypochlorite ion, sodium hypochlorite, chloride ion, or dissolved chlorine gas, about 0.4% by weight of sodium phosphate, and about 3.0% by weight of sodium magnesium fluorosilicate, wherein the concentrations of the free chlorine species present in the formulation are maintained at about 70% or greater from their initial concentration for at least two months, the viscosity of the formulation is maintained in a range of about 12000 cP to about 20000 cP for at least 18 months after preparation of the formulation, and the pH of the formulation is maintained in a range of about 6.2 to about 7.8 for at least 18 months after preparation of the formulation.

4. A method for promoting wound healing in a patient comprising applying to a wound a therapeutically effective amount of a hydrogel formulation comprising an oxidative reductive potential water solution, wherein the formulation has a pH of from about 6.2 to about 7.8, wherein the oxidative reductive potential water solution has a total amount of free chlorine species of about 10 ppm to about 400 ppm, wherein the free chlorine species is hypochlorous acid, hypochlorite ion, sodium hypochlorite, chloride ion, or dissolved chlorine gas, about 0.4% by weight of sodium phosphate, and about 3.0% by weight of sodium magnesium fluorosilicate, wherein the concentrations of the free chlorine species present in the formulation are maintained at about 70% or greater from their initial concentration for at least two months, the viscosity of the formulation is maintained in a range of about 12000 cP to about 20000 cP for at least 18 months after preparation of the formulation, and the pH of the formulation is maintained in a range of about 6.2 to about 7.8 for at least 18 months after preparation of the formulation.

5. The formulation of claim 1, wherein the total amount of free chlorine species is about 50 ppm to about 200 ppm.

\* \* \* \* \*